(12) United States Patent
Kabany

(10) Patent No.: US 12,110,617 B2
(45) Date of Patent: Oct. 8, 2024

(54) METHOD FOR PRODUCING A TEXTILE PIECE

(71) Applicant: Mohammad Kabany, Regensburg (DE)

(72) Inventor: Mohammad Kabany, Regensburg (DE)

( * ) Notice: Subject to any disclaimer, the term of this patent is extended or adjusted under 35 U.S.C. 154(b) by 862 days.

(21) Appl. No.: 16/533,217

(22) Filed: Aug. 6, 2019

(65) Prior Publication Data

US 2020/0063297 A1    Feb. 27, 2020

(30) Foreign Application Priority Data

Aug. 23, 2018    (DE) ..................... 10 2018 120 619.4

(51) Int. Cl.
*D04H 3/04*    (2012.01)
*D03D 1/00*    (2006.01)

(52) U.S. Cl.
CPC ....... *D03D 1/0088* (2013.01); *D10B 2401/16* (2013.01); *D10B 2401/18* (2013.01); *D10B 2501/06* (2013.01)

(58) Field of Classification Search
CPC .............. D03D 1/0088; D10B 2401/16; D10B 2401/18; D10B 2501/06; A61B 2560/0214; A61B 2560/0252; A61B 2562/0247; A61B 2562/029; A61B 2562/046; A61B 2562/125; A61B 5/6804; A41D 1/002

(Continued)

(56) References Cited

U.S. PATENT DOCUMENTS

2003/0145699 A1    8/2003    Kim
2010/0271212 A1*   10/2010   Page ..................... A61F 13/42
                                                         340/573.1

(Continued)

FOREIGN PATENT DOCUMENTS

DE          3910322 A1    10/1989
DE          40 00 534 C1   1/1992

(Continued)

OTHER PUBLICATIONS

International Search Report, Application No. PCT/US95/10253, patent entitled Custom Apparel Manufacturing Apparatus and Method.

*Primary Examiner* — Thuy N Pardo
(74) *Attorney, Agent, or Firm* — Michael J Gallagher; Luper Neidenthal & Logan

(57) ABSTRACT

The invention relates to a method for producing a textile piece, in particular a garment, comprising the following steps: providing a predetermination unit, which predetermines a shape and/or size and/or a textile material, providing the textile material which is formed with a textile base material, wherein, in a next step by means of a production unit, the textile base material is subdivided into at least two spatially independent textile segments which are separated by at least one cutting mark, wherein the textile segments, after their assembly, produce the textile piece predetermined by the predetermination unit, in particular a garment, wherein in a next step, electrically conductive threads are incorporated into the individual textile segments by appropriate predetermination parameters of the predetermination unit, wherein the electrically conductive threads do not intersect the cutting mark and do not run thereon, not even in at least some places.

14 Claims, 2 Drawing Sheets

(58) Field of Classification Search
USPC .............. 28/100, 102, 103; 112/313, 470.03
See application file for complete search history.

(56) References Cited

U.S. PATENT DOCUMENTS

| | | | | |
|---|---|---|---|---|
| 2012/0060735 A1* | 3/2012 | Dickerson | ................ | D05B 3/04 112/313 |
| 2012/0061441 A1* | 3/2012 | Book | ..................... | D05B 19/16 226/188 |
| 2012/0102615 A1* | 5/2012 | Dickerson | .............. | D05B 19/04 2/69 |
| 2015/0122164 A1* | 5/2015 | Dickerson | ................ | D05B 3/04 112/470.03 |
| 2015/0359485 A1* | 12/2015 | Berg | ........................ | A61B 5/24 600/388 |
| 2016/0038083 A1* | 2/2016 | Ding | .................... | A61B 5/1135 600/388 |
| 2016/0058623 A1* | 3/2016 | Lipshaw | ............... | A61F 13/085 602/75 |
| 2017/0165977 A1* | 6/2017 | Hamada | ............... | B41J 11/0095 |
| 2017/0231089 A1* | 8/2017 | Van Keymeulen | ...... | H05K 3/32 |
| 2018/0093121 A1* | 4/2018 | Matsuura | ........... | G09B 19/0038 |
| 2019/0046086 A1* | 2/2019 | Jayalath | ................ | A61B 5/1118 |
| 2019/0100859 A1* | 4/2019 | Nunn | ..................... | D01G 11/00 |
| 2019/0167489 A1* | 6/2019 | Hellmold | .............. | A61B 5/6808 |
| 2019/0281915 A1* | 9/2019 | Levi | ........................ | A41H 43/00 |
| 2021/0038437 A1* | 2/2021 | Lipshaw | ............... | A61F 13/108 |
| 2021/0084999 A1* | 3/2021 | Matsuura | ............ | G16H 20/30 |
| 2021/0153780 A1* | 5/2021 | Jayalath | ................ | A61B 5/318 |

FOREIGN PATENT DOCUMENTS

| | | |
|---|---|---|
| DE | 102004032410 A1 | 1/2006 |
| DE | 102010017684 A1 | 1/2012 |
| DE | 102017203643 A1 | 9/2018 |
| DE | 20 181 840.8-10 | 10/2022 |

* cited by examiner

METHOD FOR PRODUCING A TEXTILE PIECE

The present invention relates to a method for producing a finished textile piece (1), in particular a garment, and an apparatus for producing a finished textile piece (1), in particular a garment, or part thereof, formed of a textile material (10) according to the respective claims that follow.

A core element of the present method is, in a first step, first of all providing a predetermination unit which provides a shape and/or a size of a finished textile piece, formed of a textile material (10). For the purposes of the present invention, "providing" may be an actual haptic structural provision of a haptically structurally perceptible textile material (10), or else the textile material (10) is only virtual, that is to say in data form. For example, such a textile material (10) can be detected by data technology through various data points, which are stored in the predetermination unit. For example, such storage is within the scope of a database storage system. In a next step, a textile material (10) is provided, in the form of a textile base material (11).

This step may mean that initially either structurally or virtually the textile base material (10) is woven, for example together with the electrically conductive threads. This would mean that the electrically conductive threads are not subsequently introduced into the textile base material (11), but are already woven into the textile base material (11) during the weaving process. In this case, the electrically conductive threads can replace individual threads or thread sections of the actual textile base material (11).

Here, too, the textile base material (11) can either be structurally provided in a haptic manner or else it can be stored only virtually in the form of data in the predetermination unit and/or can be loaded into the predetermination device.

A core element of the present invention is that, in a next step, the textile base material (11) is subdivided into at least two spatially independent textile segments (210) which are separated from each other by at least one cutting mark, wherein the textile segments (210), after their assembly, produce the finished textile piece (1) predetermined by the predetermination unit, in particular a garment, wherein in a next step electrically conductive threads (4) are incorporated into the individual textile segments (210) by appropriate predetermination parameters of the predetermination unit, wherein the electrically conductive threads (4) do not intersect the cutting mark and do not run thereon, not even in at least some places.

In other words, such a cutting mark is not cut at any point, so that the entire process is based on uncut electrically conductive threads (4). Cutting through the electrically conductive threads (4) has in fact revealed that, at the cut end thereof, material defects and particular hot spots are produced during use of the electrically conductive thread (4).

Preferably, at least one cutting mark extends at least partially through the, preferably flat, textile base material (11). For example, each textile segment (210) has at least one cutting mark as part of a boundary edge.

For example, each electrically conductive thread (4) is spaced at least two millimetres from each cutting mark. This ensures that, during the cutting process, the electrically conductive thread (4) is not affected.

Further, for example, a textile segment (210) has at least two electrically conductive threads (4) preferably extending parallel to each other. A spacing between these threads can be at least one millimetre. However, the paths of the electrical threads (4) may also be curved, circular or ellipsoidal.

For example, at least two textile segment (210) sub-segments have electrically conductive threads (4) of different lengths. In this case, these threads may each have different lengths within a (textile segment (210) sub-segment and/or threads of different (textile segment (210) sub-segments have different lengths. In other words, in the above-mentioned method a cutting pattern is first applied to a preferably flat textile material (10) by means of the production unit and/or, by means of a virtual pattern, such a textile material (10) is virtually superimposed (for example, the pattern is laid over the textile material (10), for example is only laid virtually over it), wherein subsequently, this pattern is cut according to the cutting lines stored in the cutting pattern, so that the cut textile segments (210) can be subsequently joined together to then produce a finished textile piece (1) as claimed here.

The electrically conductive threads (4) are used for contacting electrically operated sensors and/or other electrically operated elements. In general, these elements can also be one or more apparatuses for measuring pressure and/or humidity.

It is possible for these sensors to be at least partially applied, for example printed, along the cutting lines on the textile segments (210) before the cutting, and to be brought into electrically conductive contact with the electrically conductive threads. After joining the individual (textile segment (210) sub-segments to the textile material (10), for example the garment, free ends of the electrically conductive threads (4) can be electrically conductively connected to a power supply unit.

Alternatively, however, the electrically operated sensors and/or other electrically operated elements can be applied to the finished textile piece (1), for example the garment, only after the finished textile piece (1) has been produced.

The apparatus for measuring pressure and/or humidity described here inter alia also comprises at least one sensor for measuring pressure and/or humidity, wherein the sensor comprises at least one capacitor with at least two electrodes, which are arranged relative to each other, in particular in a horizontal direction, along and on an, in particular flexible, support material, wherein at least one dielectric layer is arranged between the electrodes.

The horizontal direction is preferably a main extension direction of the flexible support material. The support material may be the textile base material. In this context, "flexible" means that the support material is bendable and thus resilient at least in some places. In particular, the support material may be a woven fabric or another clothing fabric such as, for example, a polyester. The dielectric layer thus spaces the two electrodes in a horizontal and/or in a transverse direction perpendicular thereto.

For example, at least one electrode and/or dielectric layer, at least in some places, and at least one, at least partially liquid-permeable and/or liquid-absorbing moisture layer is arranged on a side facing away from the support material, wherein thus the at least one electrode and/or dielectric layer are arranged in a transverse direction between the support material and the moisture layer such that a capacitance is at least partially changed by the liquid at least partially incident on the dielectric layer, wherein a processing unit is arranged and provided for measuring and/or storing this change so that a capacitive moisture sensor is produced.

A capacitive humidity sensor is in principle a capacitor of which the dielectric preferably consists of a hygroscopic polymer layer which takes up (absorbs) or releases (desorbs) moisture according to the humidity of the ambient air until an equilibrium state (diffusion gradient=0) is reached. The dielectric constant of the polymer material changes as a function of a moisture content.

The object of the processing unit is, inter alia, to determine the relative humidity as accurately as possible from a measured ambient temperature and the moisture-dependent capacitance value of the sensor.

According to at least one embodiment, the apparatus for measuring pressure and/or humidity comprises at least one sensor for measuring pressure and/or humidity, wherein the sensor comprises at least one capacitor with at least two electrodes, which, in particular in a horizontal direction, are arranged relative to each other along and on an, in particular flexible, support material, wherein at least one dielectric layer is arranged between the electrodes.

For example, at least one electrode and/or dielectric layer, at least in some places, and at least one, at least partially liquid-permeable and/or liquid-absorbing layer (=moisture layer) is arranged on a side facing away from the support material, wherein the at least one electrode and/or dielectric layer are arranged in a transverse direction between the support material and the moisture layer so that a capacitance is at least partially changed by the liquid at least partially incident on the dielectric layer, wherein a processing unit is configured and provided to measure and/or store this change, so that a capacitive humidity sensor is created.

The moisture layer may be formed with a dielectric material. The material of the moisture layer may be different from the material of the water-impermeable layer.

The sensor and/or the processing unit can be supplied with electrical energy by means of a battery or a fixed mains power supply. Alternatively or additionally, the generation of electrical energy for supplying the sensor and/or processing unit by means of so-called "energy harvesting" is possible. Energy harvesting (literally energy crops) refers to the recovery of small quantities of electrical energy from sources such as ambient temperature, vibrations or air flows for mobile apparatuses with low power. The structures used for this purpose are also called nanogenerators. In wireless technologies, energy harvesting avoids limitations by wired power supply or batteries.

Possibilities of energy harvesting:
Piezoelectric crystals generate electrical voltages when force is exerted, for example by pressure or vibration. These crystals can be arranged at or on the support material.
Thermoelectric generators and pyroelectric crystals gain electrical energy from temperature differences. These generators can be arranged at or on the support material.
The energy of radio waves, a form of electromagnetic radiation, can be captured and used energetically via antennas. An example of this is the passive RFIDs. These antennas may be arranged at or on the support material.
Photovoltaics, electrical energy from the ambient light.
Osmosis.

In addition, according to at least one embodiment, the sensor is a capacitive pressure sensor, wherein the processing unit is additionally configured and provided for measuring and/or storing a capacitance change of the capacitor caused by external pressure. In principle, a capacitive sensor is therefore a sensor which operates on the basis of the change in the electrical capacitance of a single capacitor or of a capacitor system. The influencing of the capacitance by the value to be detected can be done in various ways, which are primarily determined by the intended use.

Among other things, a capacitive sensor is based on two electrodes, one of which can be the surface to be measured, forming the "plates" of an electrical capacitor of which the capacitance or capacitance change is measured, which can be influenced as follows:
A plate is displaced and/or deformed by the effect to be measured, thereby changing the plate spacing and thus the electrical measurable capacitance.
The plates are rigid and the capacitance itself changes by bringing an electrically conductive material or a dielectric into immediate proximity.
The effective plate area changes by sliding the plates against each other as in a rotary capacitor.

In order to be able to better detect even small changes, the actual measuring electrode can often be surrounded by a shielding electrode which shields the inhomogeneous edge region of the electric field from the measuring electrode, thereby resulting in an approximately parallel electric field between the measuring electrodes of the usually earthed counterelectrode and the known characteristic of an ideal plate capacitor.

A capacitive pressure sensor is in particular one in which the capacitance change due to the flexing of a membrane and the resulting change in the plate spacing is evaluated as a sensor effect. For example, the membrane is the above-mentioned dielectric or else the individual capacitor electrodes, which may be designed in particular in the form of a plate. In other words, in such an embodiment a capacitive humidity sensor is combined with a capacitive pressure sensor in a novel way, but without these components forming separate elements or two separate sensors, but in the present embodiment it is a "two in one" concept in which the same sensor functions both as a moisture sensor and also as a pressure sensor.

In accordance with at least one embodiment, the support material is a woven fabric, in particular into which electrical conductor paths for electrical contacting of the sensor and the processing unit are woven.

In the context of the invention, a woven fabric is therefore a fabric which has been woven manually or mechanically on the basis of individual threads.

The electrical conductor paths can therefore additionally be integrated in a fabric in addition to the usual fibres and fabric strands or replace individual fabric strands which form the fabric mesh.

Depending on the spacing and properties of the individual threads (twisted, bulked, etc.), quite loose fabrics, such as bandage fabrics or dense fabrics such as brocade material, can be produced. For lengthwise resilience, fabrics are used in which rubber threads (more tapes used) or crinkled and bulked yarns are used as warp threads. They are stretched, processed and contract in the resting state. Bulked yarns consist of textured, i.e. crinkled synthetic fibres. The crinkling changes the properties of the synthetic fibres. The spun yarns are very resilient and voluminous and have a good thermal insulation.

For example, the support material may be part of an upholstery material of a seat, in particular a vehicle seat or an office chair. In this respect, the sensor, but preferably the entire apparatus, can be applied to the upholstery material of such a seat or can be integrated into such a material.

For example, the processing unit is configured and provided for detecting the individual humidity and pressure values and for determining from a combination of the individual moisture and pressure values at least one respective characteristic value from which it can be deduced which individual (with weight and/or size) just occupied the vehicle seat.

For example, from the pressure measurement by the processing unit, a weight of the respective person can be deduced and determined. Also, the respective moisture which the respective person delivers to the sensor can be measured, wherein the respective characteristic value is, for example, a product of the relative humidity value times the load weight determined by the processing unit.

If such a characteristic value exceeds a corresponding limit value, the processing unit can issue a warning, in particular by means of a connection to the electronics of the vehicle. This warning may mean that the seat is overcrowded or the driver is sweating too much. However, this warning can also be replaced by an appropriate indication as to which type of occupancy uses the seat. An occupancy type can be a weight classification of a respective user, or else it can be a question of whether the user is an animal, a person or even a thing. Preferably, therefore, the processing unit is integrated into a display electronics of the vehicle, but at least connectable thereto.

For this purpose, it is conceivable that the processing unit connects to a receiving unit of the vehicle, for example by means of Bluetooth or another wireless connection, and the respective identification or limit value and/or the respective warning and/or the respective identification of the user are reproduced on a display of the vehicle.

Alternatively or additionally, it is conceivable that these individual values and/or identifications can also be retrieved externally and/or displayed externally. For example, the car may be monitored for overcrowding by an external controller.

For example, by means of a data link, the processing unit may be in communication with a triggering unit of an airbag so that the processing unit can also control and/or regulate the triggering unit, in particular with regard to a triggering time of the airbag. Additionally and/or alternatively, it is possible for the processing unit to supply a controller unit of the airbag with data, for example, regarding a type of occupancy, a position and/or a weight of a user of the vehicle seat.

These data may result in the activation time and activation sequence of the airbag being adapted to the user, thereby avoiding personal injury to the user.

According to at least one embodiment, at least one electrode and/or dielectric layer is printed on the support material or on a layer, in particular a water-impermeable layer, arranged on the support material or is applied by means of a thin-film method.

This means that at least one element, preferably both the electrode and the dielectric layer, are printed on the support material or on a layer applied between the sensor and the support material, preferably an electrically non-conductive, more preferably water-impermeable layer, by means of a printing process. The printing process may be, for example, an inkjet process.

For example, the processing unit is applied to the support material in the same manner as the sensor. For this purpose, it is conceivable that the processing unit, but at least one, in particular conductive, layer of the processing unit is printed on the support material, for example.

The data communication between the processing unit and the sensor can then be produced over the above-mentioned conductor paths. These conductor paths can be woven at least partially, but preferably completely, into the woven fabric or even form individual fibres of the woven fabric itself For example, at least one electrode is made flat. That means that a thickness of the electrode is negligible compared to its surface area. Such an electrode can therefore be produced in particular by means of a printing process.

Alternatively, a thickness of at least one electrode may be at most 5 mm. For this purpose, the printing method can be applied several times, so that at least two, but preferably more, individual printing layers are stacked on top of each other.

Furthermore, the electrode can also be arranged on the support material by means of a 3D printing method.

1. FDM Method (Fused Deposition Modelling)

Alternative Names: Fused Filament Fabrication (FFF), Fused Layer Modelling (FLM)

The method refers to applying (extruding) a material in layers by means of a hot nozzle. The consumable material is located, in the form of a long wire (so-called filament), on a roller and is moved by the conveying unit into a print head, melted there and applied to a printing bed. The print head and/or printing bed are movable in three directions in this case. Plastics layers can thus be gradually applied to one another.

2. The SLS Method (Selective Laser Sintering)

In contrast to the sintering method, in which materials in powder form are bonded to one another under the action of heat, in the SLS method this takes place selectively by means of a laser (alternatively also an electron beam or an infrared beam). Therefore, only a specific part of the powder is melted together.

For this purpose, a thin powder layer is always applied to the printing bed by the coating unit. The laser (or another energy source) is then directed precisely to individual points of the powder layer in order to form the first layer of the print data. In this case, the powder is melted or fused and is then solidified again by slight cooling. The unmelted powder remains around the sintered regions and is used as supporting material. After a layer is solidified, the printing bed is lowered by a fraction of a millimetre. The coating unit moves over the printing bed and applies the next powder layer. Subsequently, the second layer of the print data is sintered by the laser (or another energy source). This produces a three-dimensional object in layers.

3. Three-Dimensional Printing (3DP)

The 3DP method functions very similarly to selective laser sintering, but instead of a directed energy source, a print head travels over the powder. Said print head deposits tiny droplets of a binding agent onto the underlying powder layers, which are thus bonded to one another. Otherwise, this method is identical to the SLS method.

4. Stereolithography (SLA)

Instead of a plastics wire or printing material in powder form, liquid resins, known as photopolymers, are used in the stereolithography method. Said resins are hardened in layers by UV radiation and therefore produce three-dimensional objects. For this purpose, the build platform is gradually lowered in the resin tank. There are also variants (so-called polyjet methods) without an entire tank of liquid resin. For this purpose, an epoxy resin is applied in droplets out of a nozzle and is immediately cured by a UV laser.

5. Laminated Object Manufacturing (LOM)

Alternative Name: Layer Laminated Manufacturing (LLM)

The method is based neither on chemical reactions nor on a thermal process. Here, a film or plate (e.g. paper) is cut along the contour by means of a separating tool (e.g. a knife or carbon dioxide laser) and the parts are bonded together in layers. The lowering of the build platform therefore produces a layered object made of bonded films lying one on top of the other.

One or more water-impermeable layers and/or also the moisture layer can be applied in the same manner and/or thickness as the electrode. According to at least one embodiment, the moisture layer completely covers the capacitor. This may mean that the moisture layer delimits and closes off the sensor to the outside, i.e. in the transverse direction, so that the sensor is arranged between the moisture layer and the support material.

According to at least one embodiment, the sensor has at least one further capacitor, which is arranged in the transverse direction below or above the capacitor and is arranged on or below this further water-impermeable layer and spaced apart from the capacitor by a further water-impermeable layer, so that a capacitor stack is formed.

The further capacitor may be constructed in the same way as the capacitor and may also be arranged in the same way as the capacitor on the further water-impermeable layer. By means of such a capacitor stack, the sensor technology can be refined in a particularly simple manner, namely insofar as it is conceivable that both sensors perform the same tasks for two sensors forming the capacitor stack, but respective measured values which, taken together, allow a mean value to be inferred are determined by the individual sensors. For example, the (relative) humidity of the environment is measured by each of the two sensors, wherein the moisture mean value is then determined from these two measured values. The same can apply correspondingly to the pressure measurement, so that the accuracy of the entire measurement, in particular a combination of the measurements of (relative) humidity and the respective pressure can be made very accurate.

According to at least one embodiment, the water-impermeable layer and/or the further water-impermeable layer at least partially form(s) the dielectric layer itself. This may mean that instead of the separate positioning of a dielectric layer next to the water-impermeable layer and/or next to the further water-impermeable layer, this dielectric layer itself is formed by the water-impermeable layer and/or the further water-impermeable layer.

Such a production of the dielectric layer by the water-impermeable layer(s) therefore forms a particularly simple and cost-effective production method for a cost-effective apparatus. Apart from that, it can basically be provided that the electrodes, the dielectric layer and the water-impermeable layer(s) are arranged in such a way that an electrical short-circuit is prevented in any case.

According to at least one embodiment, a maximum thickness of the moisture layer is at least 30% and at most 80% of the maximum thickness of the water-impermeable layer and/or the maximum thickness of the further water-impermeable layer. This not only ensures a particularly flat sensor, but also it ensures a particularly fast response time to humidity changes. The humidity acting from outside on the moisture layer therefore does not have to travel long distances to the dielectric.

Furthermore, the present invention relates to a method for measuring pressure and/or humidity, wherein, in particular, it should be noted that all the features disclosed for the apparatus described above are also disclosed for the method described here, and vice versa.

According to at least one embodiment, the method for measuring pressure and/or moisture initially comprises a first step by means of which at least one sensor for measuring pressure and/or humidity is provided, wherein the sensor has at least one capacitor with at least two electrodes, which are arranged relative to each other, in particular in a horizontal direction along and on an, in particular flexible, support material, wherein at least one dielectric layer is arranged between the electrodes.

According to the invention, at least one electrode and/or the dielectric layer, at least in some places, and at least one, at least partially liquid-permeable and/or liquid-absorbing moisture layer is arranged on a side facing away from the support material, wherein thus the at least one electrode and/or the dielectric layer is/are arranged in a transverse direction between the support material and the moisture layer, so that a capacitance is at least partially changed by the liquid at least partially incident on the dielectric layer, wherein a processing unit measures and/or stores this change, so that a capacitive humidity sensor is produced. In this case, the method described above has the same advantages and advantageous embodiments as the apparatus described above.

According to at least one embodiment, the method for producing a finished textile piece (1), in particular a garment, comprises a first step in which a predetermination unit is provided which predetermines a shape and/or size of a finished textile piece (1), wherein in a next step the textile material (10) is provided which is formed as a textile base material (11).

In a further step according to the invention, the textile base material is subdivided into at least two spatially independent textile segments which are separated by at least one cutting mark, wherein the textile segments, after their assembly, produce the textile piece predetermined by the predetermination unit, in particular a garment, wherein in a next step electrically conductive threads are incorporated into the individual textile segments by appropriate predetermination parameters of the predetermination unit, wherein the electrically conductive threads do not intersect the cutting mark and also do not run thereon, not even at least partially.

According to at least one embodiment, pattern segment subdivisions, which are in particular selected by a user, are stored in the predetermination unit, and the textile material is subdivided according to this pattern segment subdivision of the various textile segments.

The pattern segment subdivisions are therefore present either in haptically structural form, or stored virtually, that is to say only in data form, in the predetermination unit and can either be laid actually, that is to say structurally, or virtually over surface area of the textile material, so that a cutting template is produced thereby.

According to at least one embodiment, the user predetermines the shape and/or the size and/or the textile base material of the finished textile piece (1) to be manufactured, and these values are compared with corresponding values unambiguously predetermined in the predetermination unit, in particular corresponding pattern segment subdivisions, wherein after matching of these values the corresponding pattern segment subdivision is selected by the predetermination unit.

As an alternative or in addition, it is possible that, in the event of a deviation of the values predetermined by the user by at most, for example, 25%, corresponding pattern segment subdivisions suitable for this purpose are also selected. If this deviation is exceeded, the predetermination unit can preferably search independently for an alternative matching pattern segment. If there is no suitable pattern segment, it is conceivable that a new pattern segment subdivision will be stored and generated by the values which deviate significantly from known patterns.

According to at least one embodiment, the predetermination unit transmits the corresponding pattern segment subdivision to the production unit within the context of a data communication, wherein the data communication comprises a data transmission and further wherein the data transmission is based on a binary language or machine language. The pattern segment is therefore structurally haptically or purely virtually visualized by the production unit.

According to at least one embodiment, the provision of the textile material (10) comprises or is a virtual or technical loading of data of the textile material into the predetermination unit. In the sense of the invention, "virtual" can mean that a structurally present element is mapped purely in terms of data technology.

According to at least one embodiment, the further production steps are also carried out at least partially, but preferably completely, only virtually and therefore exist only in the form of data, so that, in the context of the subdivision of the textile material (10) and the incorporation of the electrically conductive threads (4) into the textile material (10), a production file which includes all relevant data necessary for the production is created by the predetermination unit and/or by the production unit.

According to at least one embodiment, the predetermination unit and/or the production unit transmit(s) this production file to a production machine for the haptic production of the finished textile piece (1), so that the manufacturing machine produces the finished textile piece (1) exactly in accordance with the data contents of the production file.

At least therefore in connection with the above-mentioned manufacturing machine, a structurally haptic method is provided.

In particular, however, it should be mentioned that the virtual method steps, each relating to structural elements (predetermination unit, production unit) which in technical terms solve the technical problem that different manufacturing specifications, for example, with regard to shape, size or texture of the textile material (10), preferably in a single production file, are transmitted to a production unit, so that not only are work steps saved by this virtual step complex before the manufacturing machine, but also the production machine can be adapted to the individual technical needs of the overall process as well as the needs of the user.

The predetermination unit may be a computer which comprises a memory chip and a computer chip. The same can apply to the production unit.

According to at least one embodiment, the cutting mark is fixed with at least one cutting point on the textile base material (11). This can also be done structurally haptically or virtually. The cutting marks may be laser marks, ride marks, mechanical marks such as scratches or perforations.

According to at least one embodiment, the finished textile piece (1) is made without rejects. This means that preferably 90%, particularly preferably 95%, more preferably 100% of the existing surface is formed by the above-mentioned textile segments on a predetermined textile base material (11). In other words, such a textile material does not comprises any surfaces free of such textile segments (no scrap). The finished textile piece (1) can therefore be produced without rejects.

Furthermore, the present invention relates to an apparatus for producing a finished textile piece (1), in particular a garment, wherein the apparatus comprises at least one predetermination unit, which is configured and intended to predetermine a shape and/or height of a textile material.

According to the invention, the apparatus comprises at least one production unit, which is configured and provided for subdividing the textile base material (11) into at least two spatially independent textile segments (210) which are separated from each other by at least one cutting mark, wherein the textile segments (210), after their assembly, produce a finished textile piece (10) predetermined by the predetermination unit, in particular a garment,—and further wherein the electrically conductive threads (4) can be incorporated into the individual textile segments (210) by appropriate predetermination parameters of the predetermination unit, wherein the electrically conductive threads (4) do not intersect the cutting marks and also do not run thereon, not even at least partially.

In this case, the apparatus described here has the same advantages and advantageous embodiments as the method described above and vice versa. In the following, the present invention will be described in more detail with reference to three figures.

Components which are the same and have the same effect are provided with the same reference signs, even if these components may be exaggerated in size.

Figure 1:
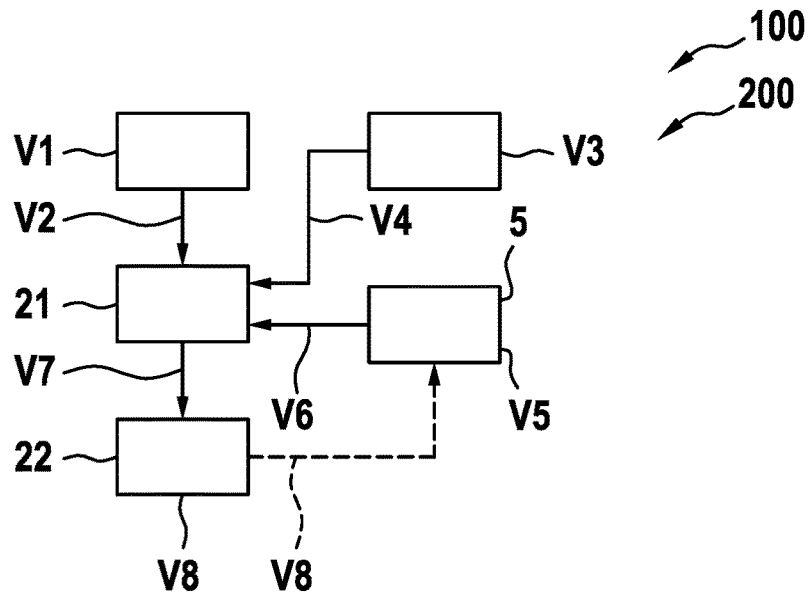
FIG. 1 shows a basic method diagram for the basic sequence of a method described here.

FIG. 1 shows firstly a first method step V1, in which firstly the material of electrically conductive threads 4 (visible in FIG. 3) and the material of a textile material 10 formed of a textile base material 11 (visible in FIG. 3) are selected from a database.

These are fed into a predetermination unit 21 in the context of a method step V2. At the same time, in the predetermination unit 21 parameters predetermined by the user for the production of the textile piece 1 desired by him are likewise loaded into the predetermination unit 21. This therefore includes steps V3 and V4.

In a step V5, certain machine conditions as well as machine characteristics of a manufacturing machine 5 are also loaded into the processing unit 21. In other words, therefore, the processing unit 21 according to the steps V1 to V6 has all the relevant data for the production of the finished textile piece 1.

The processing unit 21 now processes these data and thus creates a production program adapted to the finished textile piece 1 by means of a step V7, so that in a step V8 the production program can also be transmitted from one production unit to another or to the manufacturing machine 5. Alternatively, however, it is also possible that the program file can be transmitted to any other production machine or manufacturing machine.

Figure 2:
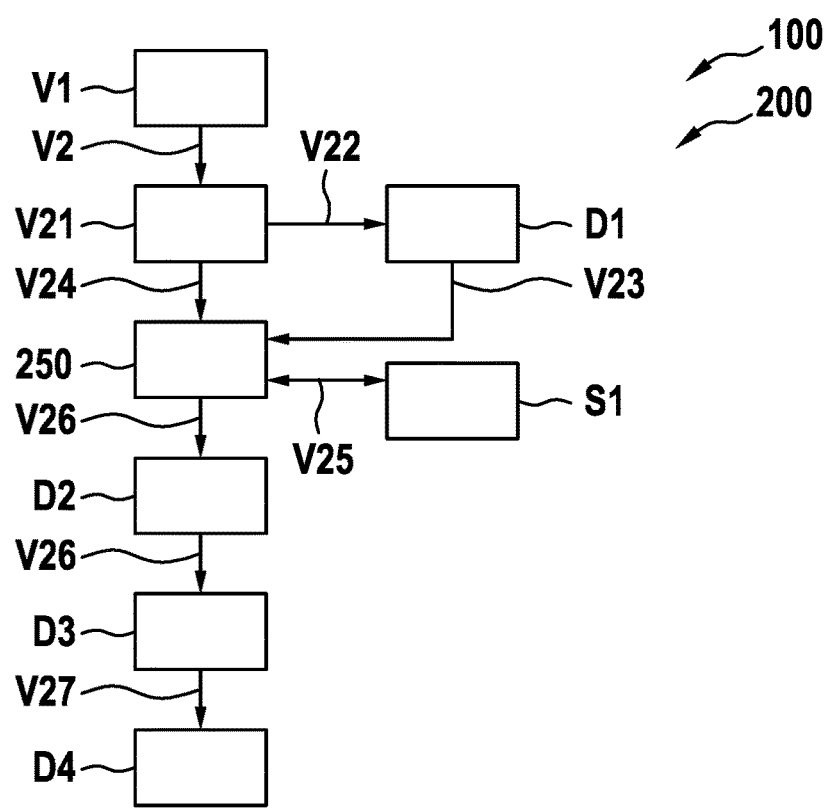
FIG. 2 shows a more detailed method diagram for the sequence of the above method according to FIG. 1.

In other words, in FIG. 1 a preferably purely virtual creation program is depicted, which, however, is absolutely necessary from a technical point of view in order to be able to operate the manufacturing machine 5. In addition, the production program is not only stored technically haptically in the processing unit 21, but is only generated thereby. FIG. 2 shows in more detail an internal data processing sequence within the predetermination unit. Again shown are the steps V1 and V2, wherein it can now be recognised that, by means of a step V2 1, data integration of all data shown in FIG. 1 is first carried out. It can also be recognised that these data are then processed, wherein a design simulation or a design verification D1 can take place in a step V22 before these data are fed back into a processing box 250 after a corresponding design simulation/verification in a step V23.

Alternatively or additionally, after the step of data integration, these data are likewise fed into the processing box 250 by means of a step V24. The processing box 250 processes and generates the corresponding cutting mark 3 (visible in FIG. 3) on the respectively underlying textile base material 11 and matches the design data then obtained by means of a step V25 in the context of a simulation/verification Si with a desired design cut profile. This design cut profile can in turn be stored in the processing unit 21.

If any deviations from a desired design cut profile are detected, in a step V26 this design can be adapted to a design profile D2 which is optimal or desired or is deposited in the processing unit 21. In a step V26, a design review check D3 is performed, wherein in a step V27 a program file D4 is then finally generated.

Figure 3:
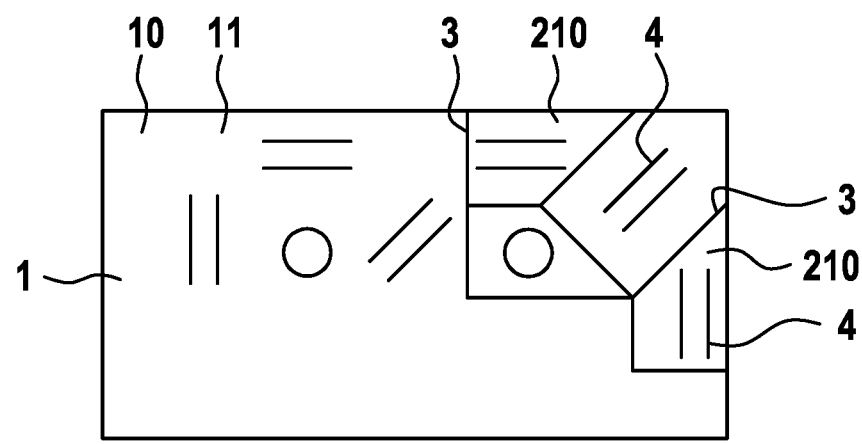
FIG. 3 shows, in a schematic top view, a segment subdivision of the textile material (10) produced prior to cutting, based on the method of FIGS. 1 and 2.

FIG. 3 schematically shows a textile base material 11 which is subdivided into the different textile segments 210. It can also be recognised that corresponding conductive threads 4 are woven within the textile segments 210 or these electrically conductive threads 4 themselves even replace a textile thread of the textile base material 11.

Furthermore, it is crucial that none of the electrically conductive threads 4 cut through the cutting marks 3 or lie on them, so that even after the corresponding cutting along the cutting marks 3, for example by means of a laser or a blade, electrically conductive threads 4 have no cut surfaces.

The applicant reserves the right to claim all features disclosed in the application documents as essential to the invention, provided that these are novel individually or in combination with respect to the prior art.

I claim:

1. A method (100) for producing a finished textile piece (1), comprising the steps of:
    a) providing a predetermination unit which predetermines a shape and/or size of a textile material (10),
    b) providing the textile material (10) which is formed as a textile base material (11),
    c) providing a production unit in which the textile base material (11) is subdivided into at least two spatially independent textile segments (210) which are separated by at least one cutting mark (3), wherein the textile segments (210) incorporate by the predetermination unit, electrically conductive threads (4) wherein the electrically conductive threads (4) do not intersect the cutting mark (3) and do not run thereon, and
    d) wherein, after assembly, a plurality of textile segments produce a finished textile piece (1) of the textile material (10) as predetermined by the predetermination unit.

2. The method acceding to claim 1, wherein a plurality of finished textile pieces (1) form a garment.

3. The method (100) according to claim 1, wherein various pattern segment subdivisions, selected by a user, may be stored in the predetermination unit.

4. The method according to claim 3, wherein the textile material (10) is subdivided into the different textile segments (210) according to the pattern segment subdivision.

5. The method (100) according to claim 3, characterised in that the user predetermines the shape and/or the size and/or the textile material (10) of the finished textile piece (1) to be produced, and these values are compared with corresponding values stored in the predetermination unit, in particular with corresponding pattern segment divisions, wherein after matching of these values the corresponding pattern segment subdivision is selected by the predetermination unit.

6. The method (100) according to claim 5, characterised in that the predetermination unit transmits the corresponding pattern segment subdivision to the production unit by means of a data communication, wherein the data communication comprises a data transmission, and further wherein the data transmission is based on a language selected from the group of languages consisting of a binary language and a machine language.

7. The method (100) according to claim 1, characterised in that the provision of the textile material (10) comprises a virtual loading of data of the textile material (10) into the predetermination unit.

8. The method (100) according to claim 1 characterised in that the subdivision of the textile material (10) and the incorporation of the electrically conductive threads (4) into the textile material (10), is predetermined by a production file created by a unit selected from the units consisting of the predetermination unit and the production unit, and wherein the production file includes all relevant data necessary for the production.

9. The method (100) according to the claim 8, characterised in that the unit selected from the group of units consisting of the predetermination unit and the production unit transmits the production file to a production machine (5) for the haptic production of the textile piece (1), such that the manufacturing machine (5) produces the textile exactly in accordance with the data contents of the production file.

10. The method (100) according to claim 1, characterised in that the cutting mark (3) is fixed with at least one cutting point on the textile material (10).

11. The method (100) according to claim 10, characterised in that the finished textile piece (1) is made without rejects.

12. An apparatus (200) for producing a textile material (10), in particular a garment, comprising:
    a) at least one predetermination unit, which is configured and intended to predetermine a shape and/or size and/or a textile material (10),
    b) at least one production unit, which is configured and provided for dividing the textile base material (11) into at least two spatially independent textile; segments (210) which are separated by at least one cutting mark (3),
    c. an assembly unit, wherein the textile segments (210), after their assembly, produce a finished textile piece (1) predetermined by the predetermination unit.

13. The apparatus of claim 12, wherein the assembly unit further assembles a plurality of finished textile pieces into a garment.

14. The apparatus of claim 12, wherein the assembly unit further incorporates at least one electrically conductive thread (4) into the individual textile segments (210) by appropriate predetermination parameters of the predetermination unit, wherein the at least one electrically conductive thread (4) does not intersect the cutting mark (3) and does not run thereon.

\* \* \* \* \*